United States Patent [19]

Fancher et al.

[11] 4,062,892
[45] Dec. 13, 1977

[54] INSECTICIDAL, MITICIDAL AND LEPIDOPTERICIDAL ACTIVE ISOTHIURONIUM COMPLEX ACIDS AND FREE BASES

[75] Inventors: Llewellyn W. Fancher, Orinda; Ashley H. Freiberg, Santa Clara, both of Calif.

[73] Assignee: Stauffer Chemical Company, Westport, Conn.

[21] Appl. No.: 775,063

[22] Filed: Mar. 7, 1977

Related U.S. Application Data

[60] Division of Ser. No. 722,464, Sept. 13, 1976, which is a continuation of Ser. No. 596,483, July 16, 1975, abandoned, which is a continuation of Ser. No. 456,103, March 29, 1974, abandoned.

[51] Int. Cl.$^2$ .............................................. C07C 127/26
[52] U.S. Cl. .................... 260/564 E; 260/380; 260/399; 260/456 A; 260/501.14; 260/925; 424/199; 424/303; 424/306; 424/312; 424/314; 424/326
[58] Field of Search .......... 260/564 E, 501.14, 456 A, 260/399, 925, 380

[56] References Cited

U.S. PATENT DOCUMENTS

| | | | |
|---|---|---|---|
| 3,093,666 | 6/1963 | Du Brow | 260/564 E |
| 3,248,426 | 4/1966 | Dvornik | 260/564 E |

OTHER PUBLICATIONS

Chemical Abstracts, vol. 60, column 7919(e).

*Primary Examiner*—Gerald A. Schwartz
*Attorney, Agent, or Firm*—Michael J. Bradley

[57] ABSTRACT

Compound having the formula

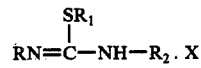

wherein R can be selected from the group consisting of benzhydryl and lower alkyls having from about 5 to about 8 carbon atoms; $R_1$ can be selected from the group of alkenyl, methyl thiomethyl, aryl, aralkyl, substituted aralkyl, cycloalkyl and lower alkyls, having from about 1 to about 6 carbon atoms; $R_2$ can be selected from the group consisting of alkenyl, aryl, aralkyl, methyl thiomethyl, cycloalkyl and lower alkyls, having from about 5 to about 10 carbon atoms and X can be selected from the group consisting of organic acids, inorganic acids or is non-existant, thus forming a free base, the organic and inorganic acids are preferably those selected from the group consisting of HI, HBr, HCl, $H_2SO_4$, $(COOH)_2$, Chrysanthemumic acid, $HCO_2CH_3$

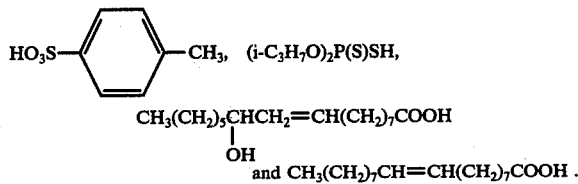

These compounds are active insecticides, miticides and lepidoptericides which can be applied to insects, mites or lepidoptera at any stage of development.

2 Claims, No Drawings

INSECTICIDAL, MITICIDAL AND LEPIDOPTERICIDAL ACTIVE ISOTHIURONIUM COMPLEX ACIDS AND FREE BASES

This is a division, of application Serial No. 722,464 filed Sept. 13, 1976, which is a continuation of application Ser. No. 596,483 filed July 16, 1975 now abandoned which is a continuation of application Ser. No. 456,103 filed Mar. 29, 1974 now abandoned.

DESCRIPTION OF THE INVENTION

The present invention is a novel group of compounds which may generally be described as certain isothiuronium salts and free bases thereof, which are active insecticides, miticides and lepidoptericides. Compounds of the present invention are represented by the generic formula:

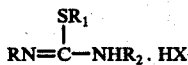

wherein R, $R_1$, $R_2$ and X are as defined above with the acidic H of X being shown for purposes of the reaction. In general, two methods of synthesis are used in the present disclosure.

The structure shown above is for convenience. Normally, these compounds are mixtures of tautomeric forms, i.e.:

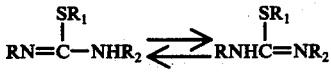

sometimes represented by:

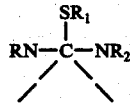

Two methods of synthesis are used in the present disclosure:

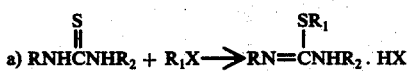

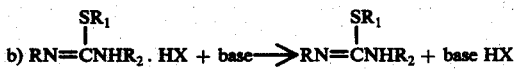

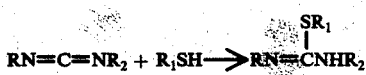

In many instances, the free base form of an isothiourea is unstable and cannot be isolated as such. In the present case, however, the free-bases appear to be reasonably stable and can be isolated.

Compounds useful in this invention are those compounds having the formula

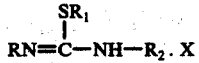

wherein R can be selected from the group consisting of benzhydryl and lower alkyls having from about 5 to about 8 carbon atoms; $R_1$ can be selected from the group of alkenyl, methyl thiomethyl, aryl, aralkyl, substituted aralkyl, cycloalkyl and lower alkyls, having from 1 to about 6 carbon atoms; $R_2$ can be selected from the group consisting of alkenyl, aryl, aralkyl, methyl thiomethyl, cycloalkyl and lower alkyls, having from about 5 to about 10 carbon atoms and X can be selected from the group consisting of organic acids, inorganic acids or is nonexistant, thus forming a free base, the organic and inorganic acids are preferably those selected from the group consisting of HI, HBr, HCl, $H_2SO_4$, $(COOH)_2$, Chrysanthemumic acid,

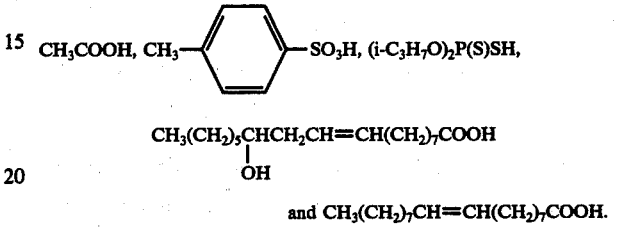

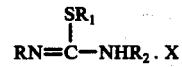

and $CH_3(CH_2)_7CH=CH(CH_2)_7COOH$.

Compounds defined by the formula $$RN=\overset{SR_1}{\underset{|}{C}}-NHR_2 \cdot X$$

wherein R can be selected from the group consisting of benzhydryl and lower alkyls having from about 5 to about 8 carbon atoms; $R_1$ can be selected from the group of alkenyl, methyl thiomethyl, aryl, aralkyl, substituted aralkyl, cycloalkyl and lower alkyls, having from 2 to about 6 carbon atoms; $R_2$ can be selected from the group consisting of alkenyl, aryl, aralkyl, methyl thiomethyl, cycloalkyl and lower alkyls, having from about 5 to about 10 carbon atoms and X can be selected from the group consisting of organic acids, inorganic acids or is non-existant, thus forming a free base, the organic and inorganic acids are preferably those selected from the group consisting of HI, HCl, $H_2SO_4$, $(COOH)_2$, Chrysanthemumic acid,

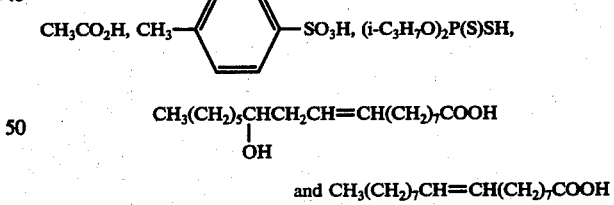

and $CH_3(CH_2)_7CH=CH(CH_2)_7COOH$ are novel compounds of this invention.

Preparation of the compounds of this invention are illustrated by the following examples:

EXAMPLE 1

S-Ethyl-1,3-di-n-heptyl-2-isothiuronium hydroiodide 13.7 g. (0.05 M) of 1,3-di-n-heptyl-2-thiourea was slurried in 30 ml. of ethanol (2B). To the mixture was added 8.3 g. (0.05 M) of ethyl iodide and the whole was refluxed, on the steam-bath, for one hour. The solvent was stripped off under vacuum leaving a highly viscous liquid, $N_d^{30}$ 1.5336. The yield was 21.1 g. (99% of theory). Structure confirmation of the above named compound was done by N.M.R.

EXAMPLE 2

S-Ethyl-1,3-di-n-heptyl-2-isothiourea (Free base of isothiuronium of Example 1)

21.5 g. (0.05 M) of S-ethyl-1,3-di-n-heptyl-2-isothiuronium hydrogen iodide was thoroughly mixed with 50 ml. of triethylamine. The mixture became warm and after cooling to room temperature, solid triethylamine hydrogen iodide was filtered off and rinsed with 20 ml. of additional triethylamine. The filtrate and washings were combined and the triethylamine removed under vacuum by means of a rotary evaporator. The product, a thin liquid, weighed 15.0 g. (95% of theory), $N_D^{30}$ 1.4805. The structure (as above) was confirmed by N.M.R.

EXAMPLE 3

S-Ethyl-1,3-di-n-heptyl-2-isothiuronium hydrobromide 4.1 g. (0.015 M) of 1,3-di-n-heptyl-2-thiourea was slurried in 10 ml. of ethanol (2B). To this mixture was added 2.2 g. (0.02 M) of ethylbromide which was then refluxed on the steam-bath for 2.5 hours. After vacuum stripping, there was obtained 5.3 g. (100% of theory) of viscous liquid, $N_D^{30}$ 1.5181. The structure (as above) was confirmed by N.M.R.

EXAMPLE 4

S-Ethyl-1,3-di-n-heptyl-2-isothiuronium hydrochloride 3.3 g. (0.011 M) of S-ethyl-1,3-di-n-heptyl-2-isothiourea base was dissolved in 10 ml. of ethanol (2B) and cooled to 5° C. To this cold solution was added a mixture of 1.2 ml. (0.015 M) of concentrated hydrochloric acid dissolved in 5 ml. of ethanol (2B), with cooling below 10° C. The mixture was evaporated under vacuum and the residue slurried in 15 ml. of acetone and re-evaporated. The slurrying and reevaporation was repeated with 15 ml. of ether. The final product, a viscous liquid, weighed 3.7 g. (92% of theory), $N_D^{30}$ 1.5052. Structure confirmation (as above) was by N.M.R.

EXAMPLE 5

S-Ethyl-1,3-di-n-heptyl-2-isothiuronium hydroacetate 9.9 g. (0.033 M) of S-ethyl-1,3-di-n-heptyl-2-isothiourea base was slurried in 25 ml. of benzene. With stirring, 2 g. (0.033 M) of glacial acetic acid was added portion-wise below 36° C. After standing overnight at ambient temperature, the solvent was stripped off under vacuum to give 12 g. (100% of theory) of viscous liquid, $N_D^{30}$ 1.4826. Structure confirmation (as above) was by N.M.R.

EXAMPLE 6

S-Ethyl-1,3-di-n-heptyl-2-isothiuronium hydro chrysanthemumate 6.0 g. (0.02 M) of S-ethyl-1,3-di-n-heptyl-2-isothiourea base was mixed with a solution of 3.4 g. (0.02 M) of Chrysanthemumic acid dissolved in 25 ml. of n-hexane by warming slightly. The mixture was stripped of solvent under vacuum. The viscous product weighed 9.4 g. (100% of theory), $N_D^{30}$ 1.4920. Structure confirmation, (as above) was by N.M.R.

EXAMPLE 7

S-Ethyl-1-t-octyl,3-octyl-2-isothiourea (Free base of the isothiuronium of Example 3)

7.9 g. (0.17 M) of S-ethyl-1-t-octyl,3-octyl-2-isothiuronium hydrogen iodide was well mixed with 25 ml. of triethylamine. After cooling to room temperature, the solid Et₃H.HI was filtered off and rinsed with 15 ml. of benzene. The filtrate and washings were combined and the excess Et₃N and benzene were removed under vacuum. The thin liquid product weighed 4.9 g. (89% of theory), $N_D^{30}$ 1.4758. Structure confirmation (as above) was by N.M.R.

EXAMPLE 8

S-Ethyl-1,3-di-n-octyl-2-isothiourea 6.8 g. (0.015 M) of S-ethyl-1,3-di-n-octyl-2-isothiuronium hydrogen iodide was dissolved in 50 ml. of benzene, the solution transferred to a separatory funnel and 80 ml. of 1% sodium hydroxide solution added. After thorough mixing, the mixture was filtered to break the emulsion formed, then transferred to a separatory funnel, the lower basic aqueous layer was removed and the benzene phase washed once with 25 ml. of dilute sodium chloride solution. After drying over anhydrous magnesiumsulfate and filtering, the solvent was removed under vacuum leaving 3.9 g. (79% of theory) of a light liquid, $N_D^{30}$ 1.4726. Structure confirmation (as above) was by N.M.R.

EXAMPLE 9

S-n-Pentyl-1-n-pentyl,3-n-hexyl-2-isothiourea 12.6 g. (0.026 M) of S-n-pentyl-1-n-pentyl,3-n-hexyl-2-isothiuronium hydrogen iodide was dissolved in 75 ml. of benzene, the solution transferred to a separatory funnel and 156 ml. of a 1% sodium hydroxide solution added. After thorough mixing, the two phases were allowed to separate and the lower aqueous phase removed. The benzene layer was washed once with 50 ml. of dilute sodium chloride solution, dried over anhydrous magnesium sulfate, filtered and the solvent removed under vacuum. The thin liquid product weighed 8.7 g. (100% of theory), $N_D^{30}$ 1.4802. Structure confirmation of the above named compound was by N.M.R.

EXAMPLE 10

S-n-butyl-1-n-heptyl,3-n-octyl-2-isothiourea

Following an identical procedure as was used in Example (2), 8.1 g. (0.0165 M) of S-n-butyl-1-n-heptyl,3-n-octyl-2isothiuronium hydrogen iodide and 25 ml. of Et₃N, yielded after work-up, 5.9 g. (100% of theory) of thin liquid product, $N_D^{30}$ 1.4751. Structure confirmation of the above named compound was by N.M.R.

EXAMPLE 11

S-i-Pentyl-1-n-octyl,3-n-hexyl-2-isothiourea

Following an identical procedure as was used in Example (2) and (10), 6.6 g. (0.14 M) of S-i-pentyl-1-n-octyl,3-n-hexyl-2-isothiuronium hydrogen iodide and 25 ml. of Et₃N, yielded after work-up 4.8 g. (100% of theory) of thin liquid product, $N_D^{30}$ 1.4695. Structure confirmation of the above named compound was by N.M.R.

EXAMPLE 12

S-Phenyl-1,3-di-n-heptyl-2-isothiourea 4.8 g. (0.02 M) of 1,3-di-n-heptyl carbodiimide and 2.2 g. (0.02 M) of thio-penol were mixed at room temperature. The reaction was slowly exothermic and the temperature rose to 48° C, then gradually diminished. After standing at ambient temperature over-night the carbodiimide I.R. band at 2140 cm$^{-1}$ had disappeared indicating the reaction to be complete. After stripping on the steam-bath for 0.5 hrs. to remove volatiles, there was obtained 6.2 g. (89% of theory) of liquid product, $N_D^{30}$ 1.5283. Structure confirmation of the above named compound was by N.M.R.

EXAMPLE 13

S-(4'-chlorophenyl)-1,3-di-n-heptyl-2-isothiourea

By essentially the same procedure as was used in Example (12), 4.8 g. (0.02 M) of 1,3-di-n-heptyl carbodiimide and 2.9 g. (0.02 M) of 4-chlorothiophenol gave after reaction 7.1 g. (92% of theory) of liquid product, $N_D^{30}$ 1.5418. Structure confirmation of the above named compound was by N.M.R.

Other compounds can be prepared in an alogous manner, starting with the appropriate materials as outlined above. Following is a table of compounds representative of those embodied in the present invention. Compound numbers have been assigned to them and are used for identification throughout the balance of this specification.

TABLE I $$RN=\underset{\underset{SR_1}{|}}{C}-NH-R_2 \cdot X$$

| Compound Number | R | $R_1$ | $R_2$ | X |
|---|---|---|---|---|
| 1 | $C_7H_{15}$ | $C_2H_5$ | $C_7H_{15}$ | HI |
| 2 | $C_7H_{15}$ | $C_2H_5$ | $C_7H_{15}$ | HBr |
| 3 | $C_7H_{15}$ | $C_2H_5$ | $C_7H_{15}$ | HCl |
| 4 | $[C_7H_{15}$ | $C_2H_5$ | $C_7H_{15}]_2$ | $H_2SO_4$ |
| 5 | $C_7H_{15}$ | $CH_3$ | $C_7H_{15}$ | HI |
| 6 | $C_7H_{15}$ | $n-C_3H_7$ | $C_7H_{15}$ | HI |
| 7 | $C_7H_{15}$ | $n-C_4H_9$ | $C_7H_{15}$ | HI |
| 8 | $C_7H_{15}$ | $C_5H_{11}$ | $C_7H_{15}$ | HI |
| 9 | $C_7H_{15}$ | $C_6H_{13}$ | $C_7H_{15}$ | HBr |
| 10 | $C_7H_{15}$ | $C_2H_5$ | $C_8H_{17}$ | HI |
| 11 | $C_7H_{15}$ | $C_2H_5$ | $C_5H_{11}$ | HI |
| 12 | $C_7H_{15}$ | $i-C_3H_7$ | $C_7H_{15}$ | HI |
| 13 | $C_7H_{15}$ | sec.-$C_4H_9$ | $C_7H_{15}$ | HI |
| 14 | $C_7H_{15}$ | $C_2H_5$ | $C_7H_{15}$ | — |
| 15 | $C_7H_{15}$ | $C_2H_5$ | $C_7H_{15}$ | $CH_3CO_2H$ |
| 16 | $C_7H_{15}$ | $i-C_5H_{11}$ | $C_7H_{15}$ | HI |
| 17 | $C_7H_{15}$ | $i-C_4H_9$ | $C_7H_{15}$ | HI |
| 18 | $C_7H_{15}$ | $-CH_2CH=CH_2$ | $C_7H_{15}$ | HBr |
| 19 | $C_7H_{15}$ | $C_2H_5$ | $C_6H_{13}$ | HI |
| 20 | $C_7H_{15}$ | $CH_2SCH_3$ | $C_7H_{15}$ | HCl |
| 21 | $C_7H_{15}$ | $C_2H_5$ | $-\underset{\underset{CH_3}{\|}}{CH}(CH_2)_4CH_3$ | HI |
| 22 | $C_7H_{15}$ | $n-C_3H_7$ | $n-C_5H_{11}$ | HI |
| 23 | $C_7H_{15}$ | $i-C_4H_9$ | $n-C_5H_{11}$ | HI |
| 24 | $C_7H_{15}$ | $n-C_5H_{11}$ | $n-C_5H_{11}$ | HI |
| 25 | $C_7H_{15}$ | $n-C_4H_9$ | $C_8H_{17}$ | HI |
| 26 | $C_7H_{15}$ | $n-C_5H_{11}$ | $C_8H_{17}$ | HI |
| 27 | $C_7H_{15}$ | $n-C_2H_5$ | $i-C_5H_{11}$ | HI |
| 28 | $C_7H_{15}$ | $CH_3$ | $C_8H_{17}$ | HI |
| 29 | $C_7H_{15}$ | $n-C_4H_9$ | $-CH_2CH=CH_2$ | HI |
| 30 | $C_7H_{15}$ | $C_2H_5$ | $t-C_5H_{11}$ | HI |
| 31 | $C_7H_{15}$ | $C_2H_5$ | $t-C_8H_{17}$ | HI |
| 32 | $C_7H_{15}$ | $C_2H_5$ | $C_7H_{15}$ | Chrysanthemumic Acid |
| 33 | $C_8H_{17}$ | $C_2H_5$ | $C_8H_{17}$ | HI |
| 34 | $C_7H_{15}$ | $C_5H_{11}$ | $t-C_5H_{11}$ | HI |
| 35 | $C_7H_{15}$ | $C_5H_{11}$ | $t-C_8H_{17}$ | HI |
| 36 | $C_7H_{15}$ | $C_5H_{11}$ | $n-C_4H_9$ | HI |
| 37 | $C_5H_{11}$ | $C_5H_{11}$ | $C_8H_{17}$ | HI |
| 38 | $C_5H_{11}$ | $C_5H_{11}$ | $C_8H_{17}$ | HI |
| 39 | $C_5H_{11}$ | $C_5H_{11}$ | $C_6H_{13}$ | HI |
| 40 | $C_6H_{13}$ | $C_2H_5$ | $C_6H_{13}$ | HI |
| 41 | $C_6H_{13}$ | $C_5H_{11}$ | $C_6H_{13}$ | HI |
| 42 | $C_7H_{15}$ | $C_5H_{11}$ | $i-C_3H_7$ | HI |
| 43 | $C_7H_{15}$ | $C_5H_{11}$ | $n-C_3H_7$ | HI |
| 44 | tert.-$C_8H_{17}$ | $C_2H_5$ | $n-C_8H_{17}$ | HI |
| 45 | tert.-$C_8H_{17}$ | $C_2H_5$ | $C_{10}H_{21}$ | HI |
| 46 | $C_7H_{15}$ | $C_2H_5$ | $C_7H_{15}$ | $(COOH)_2$ |
| 47 | $[C_7H_{15}$ | $C_2H_5$ | $C_7H_{15}]_2$ | $(COOH)_2$ |
| 48 | $C_7H_{15}$ | $C_2H_5$ | $C_7H_{15}$ | 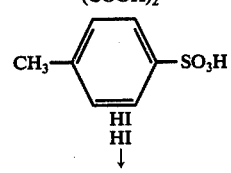 |
| 49 | $n-C_8H_{17}$ | $C_2H_5$ | $C_6H_{13}$ | HI |
| 50 | $n-C_8H_{17}$ | $i-C_5H_{11}$ | $C_6H_{13}$ | HI |
| 51 | $C_7H_{15}$ | $C_2H_5$ | $C_7H_{15}$ | ↓ |

$$X = CH_3(CH_2)_5\underset{\underset{OH}{\|}}{CH}CH_2CH=CH(CH_2)_7COOH$$

| 52 | $C_7H_{15}$ | $C_2H_5$ | $C_7H_{15}$ | ↓ |

TABLE I-continued $$RN=\underset{\underset{}{|}}{C}-NH-R_2 \cdot X$$
$$\text{with } SR_1 \text{ on C}$$

| Compound Number | R | $R_1$ | $R_2$ | X |
|---|---|---|---|---|
| | | | $X = CH_3(CH_2)_7CH=CH(CH_2)_7COOH$ | |
| 53 | $C_7H_{15}$ | $C_2H_5$ | –C₆H₄–CH₃ (tolyl) | HI |
| 54 | $C_7H_{15}$ | –CH₂–C₆H₅ (benzyl) | $C_7H_{15}$ | HCl |
| 55 | $C_7H_{15}$ | thiacyclohexyl (S-containing ring) | $C_7H_{15}$ | HI |
| 56 | $C_7H_{15}$ | $C_2H_5$ | $C_7H_{15}$ | $(i-C_3H_7O)_2P(S)SH$ |
| 57 | $C_7H_{15}$ | $C_2H_5$ | sec.-$C_8H_{17}$ | HI |
| 58 | $C_8H_{17}$ | $C_2H_5$ | i-$C_5H_{11}$ | HI |
| 59 | $C_8H_{17}$ | $C_2H_5$ | sec.-$C_7H_{15}$ | HI |
| 60 | $C_8H_{17}$ | $C_2H_5$ | sec.-$C_8H_{17}$ | HI |
| 61 | $C_7H_{15}$ | n-$C_5H_{11}$ | sec.-$C_8H_{17}$ | HI |
| 62 | $C_6H_{13}$ | $C_2H_5$ | $C_9H_{19}$ | HI |
| 63 | $C_6H_{13}$ | $C_2H_5$ | sec.-$C_8H_{17}$ | HI |
| 64 | $C_6H_{13}$ | $C_2H_5$ | sec.-$C_7H_{15}$ | HI |
| 65 | $C_7H_{15}$ | $C_6H_{13}$ | $C_4H_9$ | HBr |
| 66 | $C_7H_{15}$ | tolyl (–C₆H₄–CH₃) | $C_7H_{15}$ | — |
| 67 | t-$C_8H_{17}$ | $C_2H_5$ | $C_8H_{17}$ | — |
| 68 | $C_7H_{15}$ | –CH₂–C₆H₄(m-CH₃) | $C_7H_{15}$ | HCl |
| 69 | $C_8H_{17}$ | $C_2H_5$ | $C_8H_{17}$ | — |
| 70 | $C_5H_{11}$ | $C_5H_{11}$ | $C_6H_{13}$ | — |
| 71 | $C_7H_{15}$ | $C_4H_9$ | $C_8H_{17}$ | — |
| 72 | $C_8H_{17}$ | i-$C_5H_{11}$ | $C_6H_{13}$ | — |
| 73 | $C_7H_{15}$ | $CH_3$ | tert.-$C_8H_{17}$ | HI |
| 74 | $C_7H_{15}$ | $CH_3$ | $C_6H_{13}$ | HI |
| 75 | $C_5H_{11}$ | $C_2H_5$ | sec.-$C_7H_{15}$ | HI |
| 76 | $C_7H_{15}$ | $C_6H_{13}$ | tert.-$C_8H_{17}$ | HBr |
| 77 | $C_7H_{15}$ | $C_5H_{11}$ | $C_6H_{13}$ | HI |
| 78 | $C_5H_{11}$ | $C_4H_9$ | sec.-$C_6H_{13}$ | HI |
| 79 | $C_3H_7$ | $C_5H_{11}$ | $C_8H_{17}$ | HI |
| 80 | $C_8H_{17}$ | $CH_3$ | $C_8H_{17}$ | HI |
| 81 | $C_8H_{17}$ | n-$C_4H_9$ | $C_8H_{17}$ | HI |
| 82 | $C_8H_{17}$ | $C_3H_7$ | $C_8H_{17}$ | HI |
| 83 | $C_8H_{17}$ | $C_4H_9$ | $C_5H_{11}$ | HI |
| 84 | $C_8H_{17}$ | $C_2H_5$ | tert.-$C_5H_{11}$ | HI |
| 85 | $C_7H_{15}$ | $C_2H_5$ | sec.-$C_6H_{13}$ | HI |
| 86 | $C_7H_{15}$ | $C_5H_{11}$ | sec.-$C_6H_{13}$ | HI |
| 87 | $C_7H_{15}$ | $C_3H_7$ | $C_8H_{17}$ | HI |
| 88 | $C_7H_{15}$ | $C_6H_{13}$ | i-$C_4H_9$ | HBr |
| 89 | $C_6H_{13}$ | $C_4H_9$ | $C_6H_{13}$ | HI |
| 90 | $C_7H_{15}$ | $C_2H_5$ | –CH(C₆H₅)–CH(C₆H₅)–CH(C₆H₅)–CH(C₆H₅)– (tetra-phenyl chain) | HI |
| 91 | $C_7H_{15}$ | $CH_3$ | (same tetra-phenyl chain as 90) | HI |

TABLE I-continued $$RN=C(SR_1)-NH-R_2 \cdot X$$

| Compound Number | R | $R_1$ | $R_2$ | X |
|---|---|---|---|---|
| 92 | $C_7H_{15}$ | $CH_2SCH_3$ | 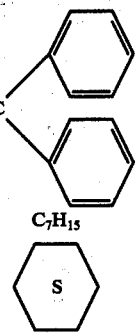 | HCl |
| 93 | tert.-$C_8H_{17}$ | $C_2H_5$ | $C_7H_{15}$ | HI |
| 94 | $C_7H_{15}$ | $C_6H_{13}$ | 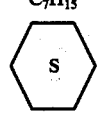 | HBr |

LEPIDOPTERICIDAL EVALUATION

Lepidoptericidal activity of the above compounds were evaluated for efficacy on various lepidopterous species as follows:

I. Salt-Marsh Caterpillar [*Estigmene acrea* (Drury)]

Test solutions are prepared as follows: Aliquots of the toxicant, dissolved in an appropriate solvent, are diluted in water to which has been added 0.0002% wetting agent (Sponto 221 ®). Test concentrations range from 0.1% to that at which 50% mortality is obtained. Sections of bitter dock (*Rumex obtusifolius*) leaves, 1-1.5 inches in length are immersed in the test solutions for 2-3 seconds and placed on a wire screen to dry. The dried leaf is placed on a moistened piece of filter paper in a petri dish and infested with five third-instar larvae. Mortality of the larvae is recorded after 7 days and the LD-50 values are expressed as percent active ingredient in the aqueous suspensions.

II. Cabbage Looper [*Trichoplusia ni* (Hubner)]

Same as the Salt-Marsh Caterpillar (I) except that leaves of Romaine lettuce (*Latuca sativa*) are utilized as the host plant rather than bitter dock.

III. Tobacco Budworm [*Heliothis virescens* (F.)]
Same as for the Cabbage Looper.

IV. Beet Armyworm [*Spodoptera exigua* (Hubner)]
Same as for the Cabbage Looper.

V. Two-Spotted Mite [*Tetranychus urticae* (Koch)]

Pinto Bean (Phaseolus sp.) plants, approximately 2-3 inches tall, are transplanted into sandy loam soil in 3-inch clay pots and infested with 50-75 mites of mixed ages. Twenty-four hours later they are sprayed, to the point of runoff, with aqueous suspensions of the toxicant. The suspensions are prepared as in previously described tests (I, II, III and IV). Test concentrations ranged from 0.05% to that at which 50% mortality is obtained. Mortality is recorded after 7 days and the LD-50 values are expressed as percent active ingredient in the aqueous suspensions.

VI. Systemic Tests

A. Salt-Marsh Caterpillar:

Aliquots of the toxicant dissolved in an appropriate solvent are diluted in water and placed in glass bottles. Concentrations of active ingredient range from 10 ppm to that at which 50% mortality is obtained. Kidney bean plants (*Phaseolus vulgaris*), supported by cotton plugs, are inserted into the solution so that the roots and major portion of the stem are completely immersed. Masses of caterpillar eggs which are nearly ready to hatch are fastened to the bean leaves. One week later mortality of the newly hatched larvae is recorded. LD-50 values are expressed as ppm of toxicant in the aqueous suspensions.

B. Two-Spotted Mite:

Preparation of the test solution and concentrations is the same as for the Salt-Marsh Caterpillar test (VI-A). Pinto bean (Phaseolus sp.) plants with expanded primary leaves are placed in the solution so that the roots and major portions of the stem are completely immersed. Immediately after, the leaves are infested with 75-100 mites of various ages. Mortality of adults, nymphs and eggs is recorded after one week, and LD-50 values are expressed as ppm of the toxicant in the aqueous suspensions.

The results by the above test procedures indicate in Table II the effective concentration at which an LD-50 control effect was achieved on the various species of lepidopterans and mites.

TABLE II

| Compound Number | SMC | SMC SYS | SMC Ovicide | CL | TBW | 2SM PE | 2SM Eggs | BAW |
|---|---|---|---|---|---|---|---|---|
| 1 | .005 | >10 | .03 | .002 | .002 | .03 | .03 | |
| 2 | .0008 | | .03 | .0008 | .003 | >.05 | >.05 | |
| 3 | .003 | | | .005 | .03 | >.05 | >.05 | |
| 4 | .001 | | | .008 | .008 | >.05 | >.05 | |
| 5 | .005 | | | .008 | .01 | >.05 | >.05 | |
| 6 | .005 | | | .008 | .008 | >.05 | >.05 | |
| 7 | .008 | | | .005 | .005 | >.05 | >.05 | |
| 8 | .008 | | | .01 | .01 | >.05 | >.05 | |
| 9 | .03 | | | .03 | .03 | >.05 | >.05 | |
| 10 | .008 | | | .003 | .01 | >.05 | >.05 | |
| 11 | .03 | | | .05 | .005 | >.05 | >.05 | |
| 12 | .003 | | | .003 | .03 | >.05 | >.05 | |
| 13 | .003 | | | .003 | .005 | >.05 | >.05 | |
| 14 | .003 | | | .003 | .03 | >.05 | >.05 | |

TABLE II-continued

| Compound Number | SMC | SMC SYS | SMC Ovicide | CL | TBW | 2SM PE | 2SM Eggs | BAW |
|---|---|---|---|---|---|---|---|---|
| 15 | .003 | | | .003 | .01 | >.05 | >.05 | |
| 16 | .008 | | | .001 | .1 | >.05 | >.05 | |
| 17 | .008 | | | .001 | .08 | >.05 | >.05 | |
| 18 | .003 | | | .003 | .05 | >.05 | >.05 | |
| 19 | .03 | | | .003 | .03 | >.05 | >.05 | |
| 20 | .003 | | | .003 | .005 | >.05 | >.05 | |
| 21 | .003 | | | .003 | .01 | >.05 | >.05 | |
| 22 | .03 | | | .03 | >.1 | >.05 | >.05 | |
| 23 | .01 | | | .01 | >.1 | >.05 | >.05 | >.1 |
| 24 | .01 | | | .01 | >.1 | >.05 | >.05 | .08 |
| 25 | .01 | | | .003 | .05 | >.05 | >.05 | .05 |
| 26 | .03 | | | .008 | | >.05 | >.05 | >.1 |
| 27 | .05 | | | | | >.05 | >.05 | |
| 28 | .03 | | | <.003 | .03 | >.05 | >.05 | >.1 |
| 29 | .05 | | | | | >.05 | >.05 | |
| 30 | .03 | | | .01 | .05 | >.05 | >.05 | .1 |
| 31 | .05 | | | .005 | .1 | >.05 | >.05 | >.1 |
| 32 | .008 | | | .005 | .008 | >.05 | >.05 | .03 |
| 33 | .03 | | | .003 | .05 | >.05 | >.05 | .1 |
| 34 | .03 | | | >.1 | .05 | >.05 | >.05 | .05 |
| 35 | .05 | | | .08 | .05 | >.05 | >.05 | .1 |
| 36 | .03 | | | .1 | .1 | >.05 | >.05 | >.1 |
| 37 | .01 | | | .05 | .08 | >.05 | >.05 | >.1 |
| 38 | .03 | | | .03 | .03 | >.05 | >.05 | >.1 |
| 39 | .03 | | | >.1 | .08 | >.05 | >.05 | >.1 |
| 40 | .05 | | | .1 | .08 | >.05 | >.05 | >.1 |
| 41 | .03 | | | .03 | .08 | >.05 | >.05 | >.1 |
| 42 | .01 | | | .03 | .08 | >.05 | >.05 | >.1 |
| 43 | .05 | | | .05 | .03 | >.05 | >.05 | >.1 |
| 44 | .008 | | | .003 | .1 | >.05 | >.05 | >.1 |
| 45 | .03 | | | .005 | .05 | >.05 | >.05 | |
| 46 | .005 | | | .005 | .1 | >.05 | >.05 | >.1 |
| 47 | .008 | | | .005 | .1 | >.05 | >.05 | >.1 |
| 48 | .005 | | | .008 | .1 | >.05 | >.05 | >.1 |
| 49 | .005 | | | .008 | .005 | >.05 | >.05 | >.1 |
| 50 | .01 | | | .01 | .05 | >.05 | >.05 | >.1 |
| 51 | .03 | | | .03 | .03 | >.05 | >.05 | >.1 |
| 52 | .03 | | | .03 | .005 | >.05 | >.05 | |
| 53 | .03 | | | .03 | .01 | .05 | .05 | |
| 54 | .05 | | | .003 | .03 | >.05 | >.05 | >.1 |
| 55 | .05 | | | .03 | .01 | >.05 | >.05 | >.1 |
| 56 | .008 | | | .008 | .01 | >.05 | >.05 | |
| 57 | .005 | | | .001 | .005 | >.05 | >.05 | |
| 58 | .03 | | | .01 | .05 | >.05 | >.05 | |
| 59 | .003 | | | .001 | .03 | >.05 | >.05 | |
| 60 | .005 | | | .001 | .01 | .03 | >.05 | |
| 61 | .005 | | | .005 | .08 | .03 | .03 | |
| 62 | >.05 | | | .005 | .05 | .03 | .03 | |
| 63 | .0008 | | | .003 | .01 | >.05 | >.05 | |
| 64 | .003 | | | .005 | .005 | >.05 | >.05 | |
| 65 | .05 | | | .05 | >.1 | >.05 | >.05 | |
| 66 | .005 | | | .03 | .01 | >.05 | >.05 | |
| 67 | .003 | | | .001 | .03 | >.05 | >.05 | |
| 68 | .03 | | | .001 | .01 | >.05 | >.05 | |
| 69 | .03 | | | .001 | .008 | >.05 | >.05 | |
| 70 | .008 | | | .03 | .01 | >.05 | >.05 | |
| 71 | .003 | | | .001 | .01 | >.05 | >.05 | |
| 72 | .008 | | | .003 | .03 | >.05 | >.05 | |
| 73 | .008 | | | .003 | .03 | >.05 | >.05 | |
| 74 | .05 | | | | | | | |
| 75 | .01 | | | .03 | .01 | >.05 | >.05 | |
| 76 | .05 | | | | | >.05 | >.05 | |
| 77 | .003 | | | .003 | .01 | >.05 | >.05 | |
| 78 | .03 | | | .03 | >.1 | >.05 | >.05 | |
| 79 | .008 | | | .008 | >.1 | >.05 | >.05 | |
| 80 | .05 | | | | .05 | >.05 | >.05 | |
| 81 | .05 | | | | | >.05 | >.05 | |
| 82 | .03 | | | .005 | .1 | .05 | .03 | |
| 83 | .005 | | | .003 | >.1 | .05 | .05 | |
| 84 | .01 | | | .008 | .03 | >.05 | >.05 | |
| 85 | .01 | | | .05 | .05 | .05 | .01 | |
| 86 | .03 | | | .05 | .1 | >.05 | >.05 | |
| 87 | .003 | | | .001 | .01 | .05 | .01 | |
| 88 | .05 | | | | | >.05 | >.05 | |
| 89 | .005 | | | .005 | .1 | >.05 | >.05 | |
| 90 | .05 | | | | | .005 | .03 | |
| 91 | .05 | | | | | .005 | >.05 | |
| 92 | >.05 | | | | | .005 | >.05 | |
| 93 | >.05 | | | | | .01 | >.05 | |
| 94 | >.05 | | | | | .03 | .03 | |

SMC = Salt-Marsh Caterpillar
SYS = Systemic
CL = Cabbage Looper
TBW = Tobacco Budworm
2SM = Two-Spotted Mite
PE = Post-embryonic
BAW = Beet Armyworm
> = greater than
< = less than The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition for example, an emulsion, suspension, or aerosol spray. While the concentration of the active pesticide in the present compositions can vary within rather wide limits, ordinarily the pesticide compound will comprise not more than about 15.0% by weight of the compositions. Preferably, however, the pesticide compositions of this invention will be in the form of solutions or suspensions containing about 0.1 to 1.0% by weight of the active pesticide compound.

What is claimed is:

1. A compound having the formula

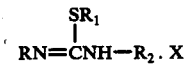

wherein R can be selected from the group consisting of benzhydryl and lower alkyls having from about 5 to about 8 carbon atoms; $R_1$ is alkenyl; $R_2$ can be selected from the group consisting of alkenyl, aryl, aralkyl, methyl thiomethyl, cycloalkyl and lower alkyls, having from about 5 to about 10 carbon atoms; and X can be selected from the group consisting of insecticidally, miticidally and lepidoptericidally acceptable acids or is non-existent.

2. A compound having the formula

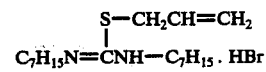

* * * * *